United States Patent [19]

Ratner

[11] Patent Number: 5,557,049

[45] Date of Patent: Sep. 17, 1996

[54] DISPOSABLE MANOMETER FOR USE WITH A CPR BAG

[75] Inventor: Jeffrey B. Ratner, Pinellas Park, Fla.

[73] Assignee: Mercury Enterprises, Inc., Clearwater, Fla.

[21] Appl. No.: 552,471

[22] Filed: Nov. 9, 1995

[51] Int. Cl.$^6$ ....................................................... G01L 7/08
[52] U.S. Cl. ......................... 73/715; 73/756; 128/204.23; 128/205.23; 128/675; 128/748
[58] Field of Search ............................. 73/715, 716, 714, 73/756; 128/204.23, 205.23, 205.24, 672, 673, 675, 748

[56] References Cited

U.S. PATENT DOCUMENTS

| | | |
|---|---|---|
| 2,271,268 | 1/1942 | Longstreet . |
| 3,975,959 | 8/1976 | Larkin . |
| 4,020,784 | 5/1977 | Greene . |
| 4,347,744 | 9/1982 | Buchanan ................................. 73/715 |
| 4,433,579 | 2/1984 | Horn ......................................... 73/715 |
| 4,821,713 | 4/1989 | Bauman . |
| 5,140,982 | 8/1992 | Bauman . |
| 5,357,951 | 10/1994 | Ratner ................................. 128/205.24 |

*Primary Examiner*—Richard Chilcot
*Assistant Examiner*—Joseph L. Felber
*Attorney, Agent, or Firm*—Herbert W. Larson

[57] ABSTRACT

A disposable manometer includes a chamber connectable to a source of CPR air pressure via a patient breathing valve and an elongated restricted passageway. The manometer includes a dial and a pointer rotatably disposed with respect to the dial to indicate the pressure sensed within a manometer chamber. The pointer has an actuator stem with a spiral-shaped protrusion coupled to a groove within an opening of a stem coupling attached at the center of a diaphragm forming one wall of the manometer chamber. Responsive to pressurized air entering the manometer chamber, the diaphragm reciprocates against the force of a biasing spring moving the stem coupling with respect to the actuator stem for the pointer so that the interaction between the spiral-shaped protrusion and the groove causes rotation of the pointer to indicate the pressure within the manometer chamber. The disposable manometer is intended to be used with a CPR bag or a patient breathing tube.

15 Claims, 3 Drawing Sheets

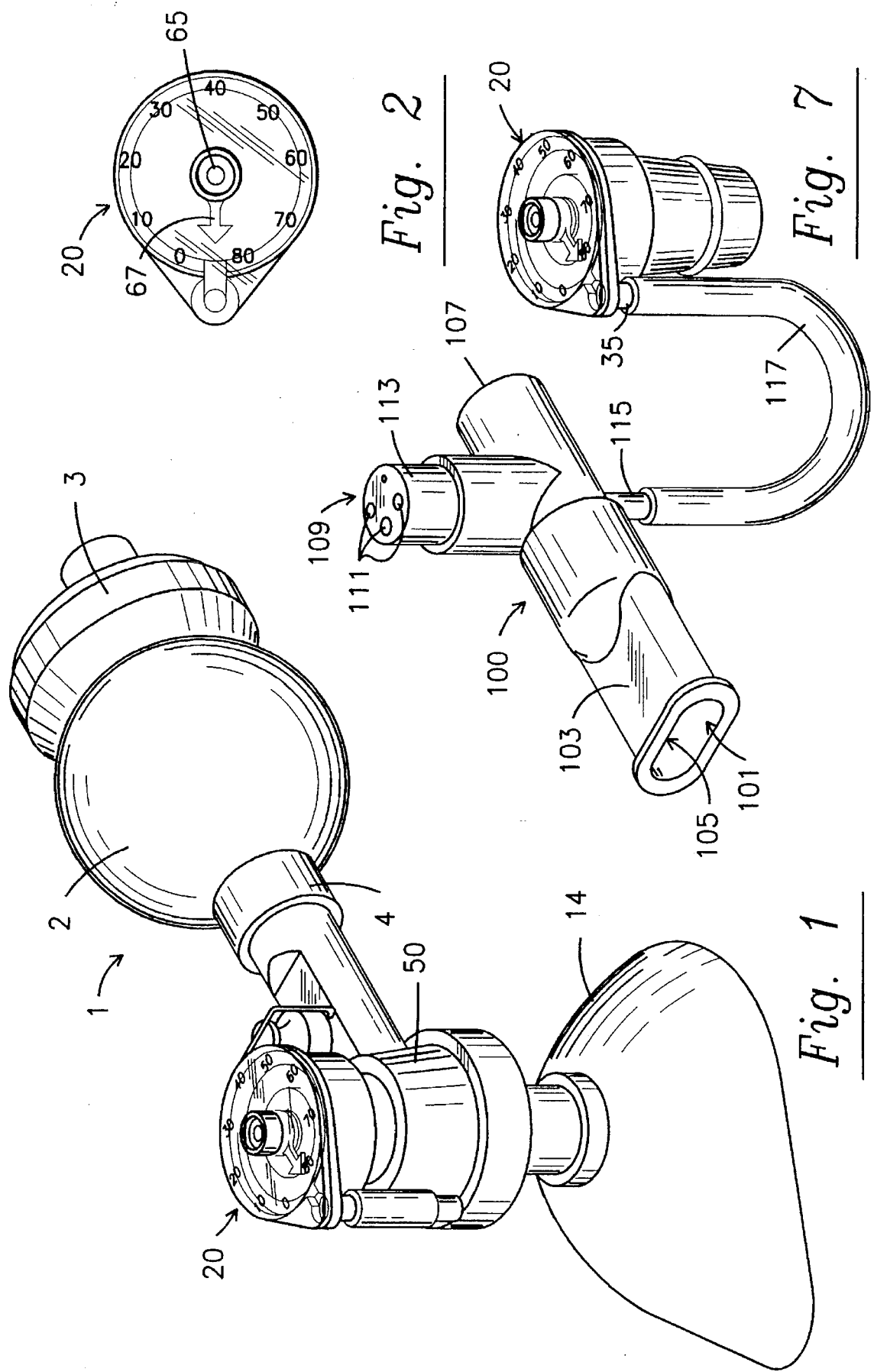

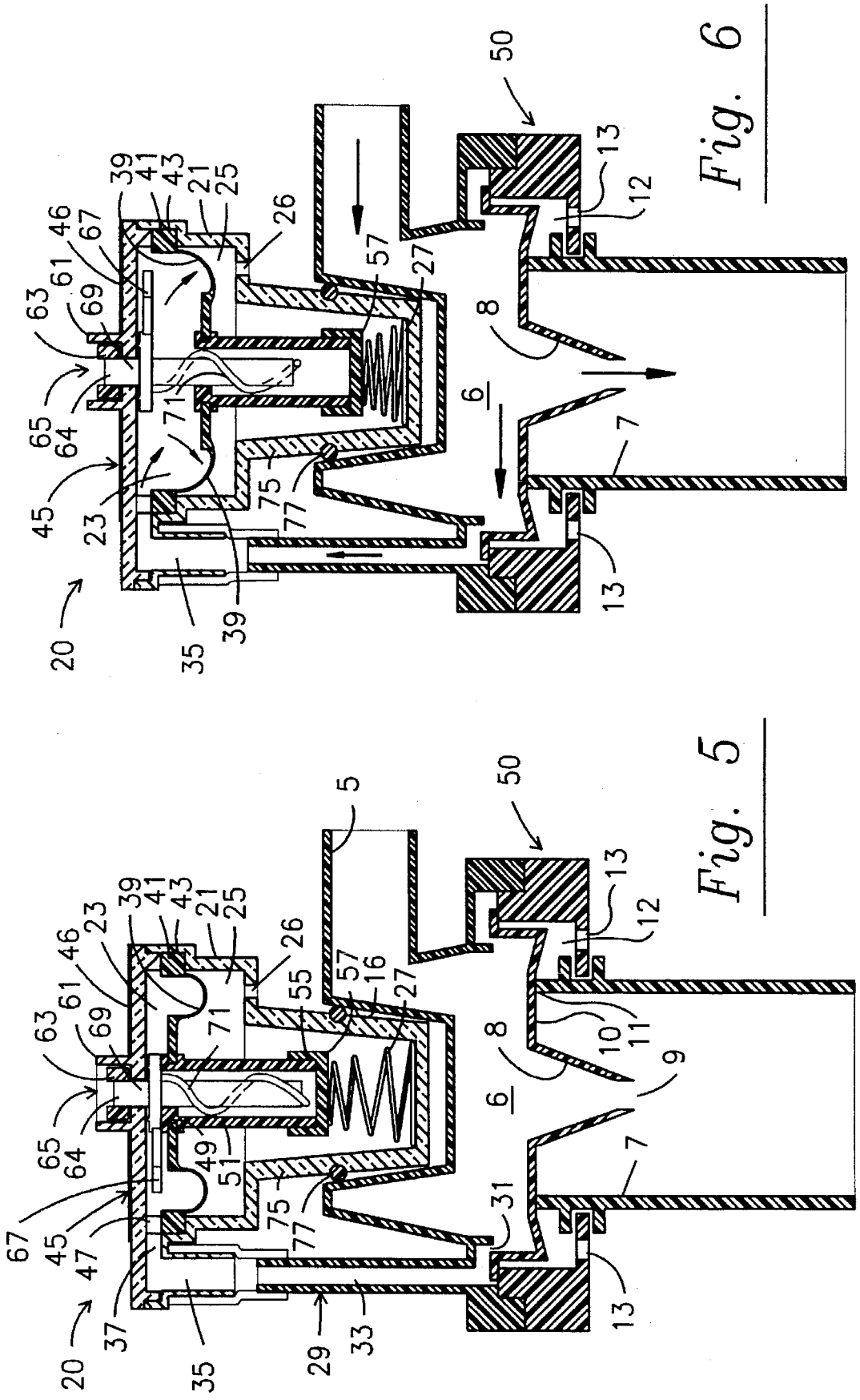

DISPOSABLE MANOMETER FOR USE WITH A CPR BAG

BACKGROUND OF THE INVENTION

The present invention relates to a disposable manometer for use with a cardio-pulmonary resuscitator CPR bag. In the prior art, manometers are known, however, Applicant is unaware of any such device including all of the features and aspects of the present invention. Applicant is aware of U.S. Pat. No. 3,975,959 to Larkin which discloses a pressure gauge including a dial with an indicator pointer connected to a cylindrical follower having projections coupled with grooves formed in a stem portion connected to a movable wall. The movable wall is exposed to a source of air pressure and reciprocates the stem portion directly responsive to changes in air pressure to cause rotation of the follower and the pointer. The present invention differs from the teachings of Larkin as contemplating a rotatable pointer carried on a stem having an external spiral-shaped projection with a fixed stem coupling carried by a diaphragm. Furthermore, the inventive disposable manometer includes an elongated restricted passageway connecting the source of pressure to the manometer chamber. This restricted passageway acts to smooth out transient fluctuations in pressure so that the operation of the pointer is much smoother than is possible in the Larkin device which has the movable wall directly exposed, without restriction, to the source of pressure, and, thus, is susceptible to every minute variation in pressure from the source thereof such that operation of the pointer of Larkin cannot be as smooth as is the case in the present invention. In addition, the diaphragm of the present invention does not leak whereas the Larkin device is a piston type device that can leak air.

Applicant is also aware of the following U.S. Patents:

U.S. Pat. No. 2,271,268 to Longstreet
U.S. Pat. No. 4,020,784 to Greene
U.S. Pat. No. 4,821,713 to Bauman
U.S. Pat. No. 5,140,982 to Bauman These references are believed to be of only general interest concerning the teachings of the present invention.

SUMMARY OF THE INVENTION

The present invention relates to a disposable manometer for use with a CPR bag. The present invention includes the following interrelated objects, aspects and features:

(1) In a first aspect, the present invention is intended for use in conjunction with a cardio-pulmonary resuscitation bag. The CPR bag includes a bulb squeezable to dispense air through a duckbill check valve to an outlet coupled to a face mask placeable over the patient's nose and mouth. When the patient exhales, the exhaled air is prevented from flowing in the reverse direction by a duckbill check valve and instead lifts the peripheral edges of the duckbill check valve to expose an exhaust port exhausting the air to atmosphere.

(2) The inventive disposable manometer is coupled to a restricted passage exposed to air expelled by the bulb so that the operator of the CPR bag may monitor the pressure of air being supplied to and from the patient. The restricted passageway evens out transient fluctuations in air pressure which are irrelevant to appropriate monitoring of the operation of the CPR bag.

(3) The disposable manometer includes a housing having an upper chamber and a lower chamber separated by a movable wall, for example, a diaphragm. The upper chamber is connected via the restricted passageway to the source of air pressure (the bulb) and the lower chamber is exhausted to atmosphere by a suitable vent. A compression spring contained within the lower chamber biases the diaphragm in the upward direction.

(4) A stem coupling is attached at the center of the diaphragm and has an opening therethrough including a generally circular portion and a groove extending radially outwardly from the circular portion. In the preferred embodiment, the stem coupling is elongated downwardly into the lower chamber and has a bottom surface engaging the compression spring.

A circular dial is provided with indicia thereon indicating a range of pressures. A pointer is rotatably disposed with respect to the dial and includes a downwardly extending actuator stem received within the generally circular portion of the opening through the stem coupling. The actuator stem also has a peripheral outwardly extending spiral-shaped protrusion received within the stem coupling groove. In this way, reciprocations of the stem coupling translate to rotations of the actuator stem as the stem coupling moves upwardly and downwardly acting upon the captured spiral-shaped protrusion of the actuator stem. The compression spring is so sized and configured that when the pressure within the upper chamber of the manometer housing is at atmospheric pressure, the pointer is aligned with the zero indicium on the dial. As pressure increases within the upper chamber causing the diaphragm and the stem coupling to move downwardly, the pointer moves along the indicia reading the pressure in the upper chamber. When the pressure is, again, released, the compression spring restores the position of the diaphragm and stem coupling and thus the position of the pointer to the zero indicium.

As such, it is a first object of the present invention to provide a disposable manometer for use with a CPR bag.

It is a further object of the present invention to provide such a device including upper and lower chambers separated by a movable diaphragm carrying a stem coupling receiving a stem portion of a pointer therefor.

It is a yet further object of the present invention to provide such a device wherein the actuator stem for the dial pointer has a spiral-shaped protrusion coupled to a groove within the stem coupling to cause reciprocations of the diaphragm to be translated to rotations of the dial pointer.

It is a yet further object of the present invention to provide such a device including an elongated restricted passageway interconnecting the source of air pressure to the upper chamber of the manometer housing so that transient fluctuations in pressure are smoothed out.

These and other objects, aspects and features of the present invention will be better understood from the following detailed description of the preferred embodiment when read in conjunction with the appended drawing figures.

BRIEF DESCRIPTION OF THE DRAWINGS

FIG. 1 shows a perspective view of a CPR bag having the inventive disposable manometer attached thereto.

FIG. 2 shows a top view of the disposable manometer.

FIG. 5 shows a cross-sectional view through the disposable manometer and a portion of the CPR bag housing with the manometer and diaphragm at an upper position thereof so that the dial pointer reads zero pressure.

FIG. 6 shows a cross-sectional view through the disposable manometer and a portion of the CPR bag housing showing the effect of air pressure within the upper chamber of the manometer housing on the position of the diaphragm and pointer and other associated structure.

FIG. 7 shows a perspective view of the inventive disposable manometer fluidly coupled to a patient breathing tube.

SPECIFIC DESCRIPTION OF THE PREFERRED EMBODIMENT

Figure 3:
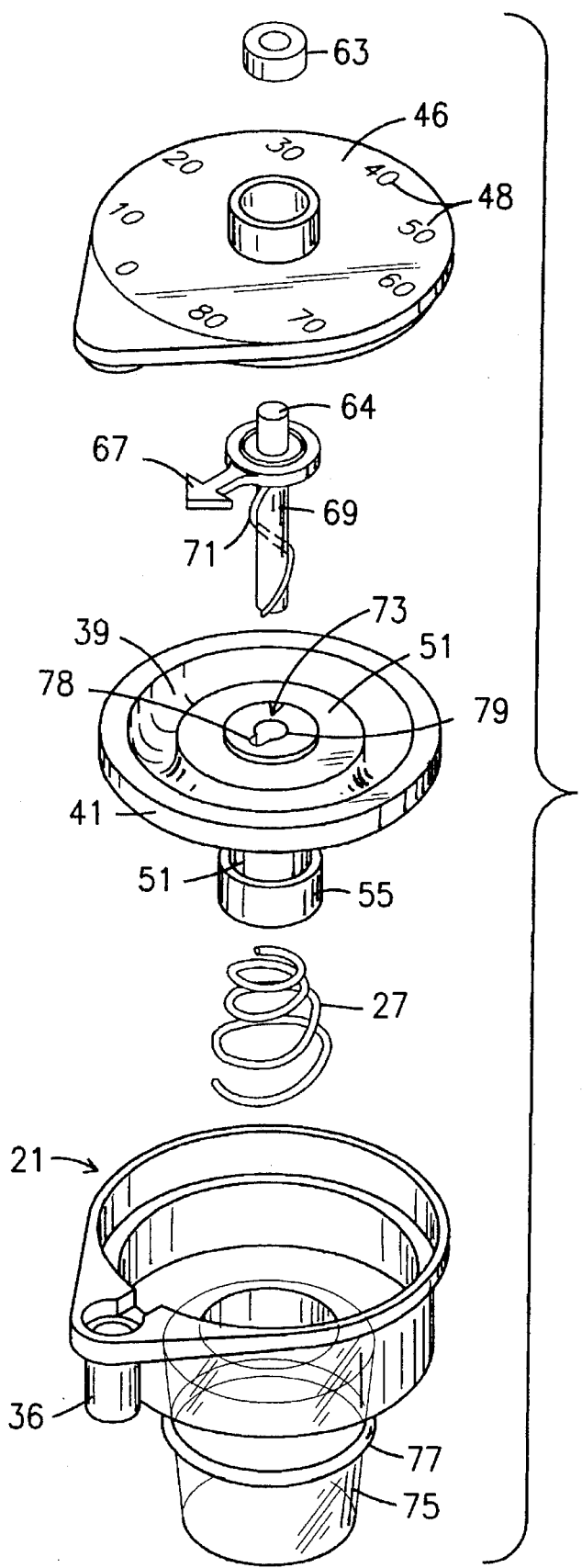
FIG. 3 shows an exploded perspective view of the disposable manometer.

With reference, first, to FIG. 1, a CPR bag is generally designated by the reference numeral 1 and is seen to include a squeeze bulb 2 connected between an inlet fitting 3 and an outlet fitting 4. As is well known to those skilled in the art, the inlet fitting 3 customarily includes a flexible inlet check valve allowing the bulb 2 to fill with air when it is in a compressed position and released, while the outlet fitting 4 customarily includes a flexible check valve allowing flow of air from the bulb 2 but not into the bulb 2. Thus, when the bulb 2 is squeezed, the check valve within the inlet fitting 2 closes and the check valve within the outlet fitting 4 opens to allow air to flow therepast. When the bulb 2 is released, the check valve in the outlet fitting 4 closes and the check valve within the inlet fitting 3 opens allowing the bulb to be filled with a fresh supply of air. This operation is well known to those skilled in the art. The outlet fitting 4 leads to a patient breathing valve 50 to passageway 5 (FIGS. 5 and 6) leading to an internal chamber 6 having an outlet 7 controlled by a duckbill-type check valve 8 having an outlet orifice 9 opened when pressure above a threshold level is within the chamber 6. When pressure in the outlet 7 is greater than pressure in the chamber 6, the opening 9 of the duckbill check valve 8 is closed to prevent reverse flow into chamber 6. When reverse flow occurs, with reference to FIGS. 5 and 6, the duckbill check valve 8 has a surface 10 resting on a seat 11 forming a portion of the outlet 7. In response to reverse flow of air into the outlet 7, the portion 10 of the duckbill check valve lifts off the seat 11 while the opening 9 of the duckbill check valve 8 remains closed thereby exposing return air flow to the chamber 12 connected to atmosphere via a series of vent ports 13. Thus, the duckbill check valve 8 actually operates as a supply and exhaust valve, supplying the patient by the outlet 7 and the mask 14 (FIG. 1) and exhausting the exhalations of the patient via the mask 14, outlet 7, chamber 12 and vent ports 13. Such operation is also customary and well known to those skilled in the art.

The inventive disposable manometer is generally designated by the reference numeral 20 and, with particular reference, first, to FIGS. 5 and 6, includes a housing 21 defining an upper chamber 23 and a lower chamber 25 which contains a compression spring 27 for a purpose to be described in greater detail hereinafter. An elongated passageway 29 interconnects the upper chamber 23 of the disposable manometer housing 21 with the chamber 6 of the CPR bag via a restricted orifice 31. The combination of the restricted orifice 31 and the elongated passageway 29 serves to even out transient fluctuations in the pressure within the chamber 6 to prevent rapid fluctuations in pressure indication as will be described in greater detail hereinafter.

The elongated passageway 29 includes a portion 33 incorporated into a patient breathing valve extension 50 of the CPR bag 1, a further passageway 35 incorporated into the disposable manometer housing 21 and an entry orifice 37 connecting the passageway 35 to the chamber 23.

With further reference to FIGS. 5 and 6 in particular, the upper chamber 23 and lower chamber 25 are separated by a movable wall such as, for example, the diaphragm 39 which includes a peripheral enlarged area 41 captured between a shoulder 43 of the housing 21 and an annular protrusion 47 of a cap 45 of the housing. The diaphragm has a central opening 49 carrying a stem coupling 51 having an internal chamber and a lower closure 55 having a bottom surface 57 which rests on the top of the compression spring 27.

The cap 45 overlies the housing 21 and closes the upper chamber 23 as best seen in FIGS. 5 and 6. As also seen in these Figures, the cap 45 has an upwardly extending annulus 61 which receives an upper portion of a pointer mechanism 65. A sleeve 63 is interposed between the annulus 61 and an upper protrusion 64 of the pointer mechanism 65 to maintain alignment of the pointer mechanism 65 therein.

Figure 4:
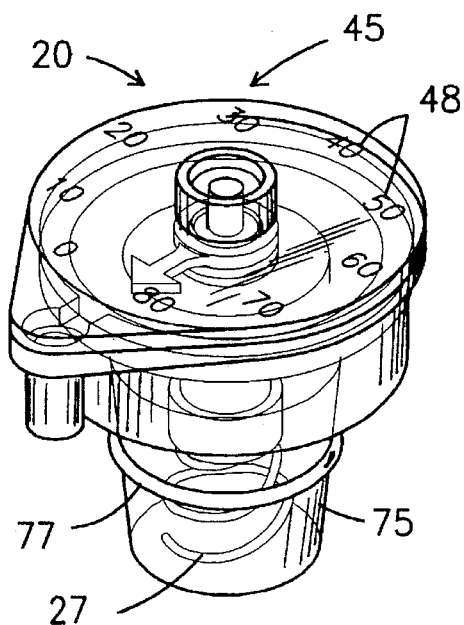
FIG. 4 shows a perspective view of the disposable manometer.

The pointer mechanism 65 includes a pointer 67 attached to an elongated stem 69 having an elongated spiral-shaped protrusion 71 extending therearound. As best seen in FIG. 3, the stem coupling 51 has a central opening 73 including a circular portion 79 and a radially outwardly extending groove 78 which receives the protrusion 71 therein while the rest of the stem 69 of the pointer mechanism 65 is slidably received within the circular portion 79 thereof. As should now be clearly understood, when the diaphragm 39 is reciprocated within the chambers 23 and 25, such reciprocations, with the protrusion 71 riding within the groove 78, cause corresponding rotations of the pointer 67. With reference to FIGS. 2, 4 and 5, when the spring 27 is in the maximum extended position shown in FIG. 5, the pointer 67 is in the appropriate position to read zero pressure. As air pressure enters the upper chamber 23 and causes displacement of the diaphragm 39 downwardly in the view of FIGS. 5 and 6 toward the position shown in FIG. 6, the pointer 67 rotates due to the reciprocation of the stem coupling 51 and the interaction between the groove 78 thereof and the protrusion 71 of the pointer mechanism 65 to cause the pointer 67 to rotate to align with the appropriate indicium indicating the pressure within the chamber 23. As the diaphragm 39 reciprocates either downwardly or upwardly, the pressure within the chamber 25 is always exposed to atmosphere via the vents 26 so that the pressure within the lower chamber 25 has no bearing on pressure indications which are indicative of pressure within the CPR bag chamber 6. As clearly shown in FIG. 3, the cap 45 has a top surface 46 having indicia 48 indicative of the pressure within the chamber 6 of the CPR bag 1 as indicated by the particular position of the arrow 67. In the preferred embodiment of the present invention, the cap 45 is transparent with the pointer 67 situated below the cap 45 within the chamber 23 so that the position of the pointer 67 is visible through the cap 45.

As best seen in FIGS. 5 and 6, the patient breathing valve 50 can conveniently include a recess 16 sized to receive a protruding portion 75 of the manometer housing 21 in an interference fit as shown. An O-ring seal 77 may be suitably employed on the protrusion 75 to facilitate the interconnection between the housing 21 and the patient breathing valve 50.

With reference to FIG. 7, a patient breathing tube is generally designated by the reference numeral 100 and includes a mouthpiece 101, an elongated housing 103 having an internal passageway 105, a closed distal end 107 and an outlet 109 comprised of orifices 111 formed on a rotatable valve fitting 113 rotatable in a manner well known to those skilled in the art to adjust the number of orifices 111 fluidly connected to the mouthpiece 101 to thereby facilitate adjustments of the resistance that is provided to the user. A sensing port 115 is provided which interconnects with the passageway 35 of the inventive disposable manometer 20 via a flexible tube 117. The patient breathing tube 100 is a device well known to those skilled in the art and is used to allow a patient to exercise their breathing function by blowing into the mouthpiece 101 and through the variable resistance outlet 109. In this environment of contemplated use, the inventive disposable manometer 20 is employed to display the pressure at which the patient may blow through the breathing tube 100. Of course, the sensing port 115 is directly fluidly connected to the passageway 105 therein.

In the preferred embodiment of the inventive disposable manometer 20, the spring 27 is made of metal and the diaphragm 39 is made of a flexible material such as rubber. The other components thereof are made of plastic, preferably in an injection molding process. Of course, other materials may suitably be employed for the various components and structures of the inventive manometer 20.

As such, an invention has been disclosed in terms of a preferred embodiment thereof which fulfills each and every one of the objects of the invention as set forth hereinabove and provides a new and useful disposable manometer for use with a CPR bag of great novelty and utility.

Of course, various changes, modifications and alterations in the teachings of the present invention may be contemplated by those skilled in the art without departing from the intended spirit and scope thereof. As such, it is intended that the present invention only be limited by the terms of the appended claims.

What is claimed is:

1. In combination with a CPR bag having an inlet, an outlet attached to a patient breathing valve and a CPR bag chamber therebetween, a manometer for sensing and displaying air pressure expelled from said CPR bag chamber comprising:
   a) a housing having an upper chamber and a lower chamber separated by a movable wall, said movable wall carrying a stem coupling having an opening with an outwardly extending groove and a bottom surface engaging a compression spring within said lower chamber;
   b) said upper chamber being upwardly closed by a cap having pressure indicating indicia thereon, and said cap having a pointer mechanism rotatably mounted thereon and including a pointer alignable with said indicia to indicate pressure in said upper chamber, said pointer mechanism including a downwardly depending actuator stem having a spiral-shaped projection thereon, said actuator stem inserted into said stem coupling opening with said spiral-shaped projection engaged within said groove, whereby reciprocations of said stem coupling translate to rotations of said pointer;
   c) said upper chamber being fluidly connected to said patient breathing valve via a restricted passageway and said lower chamber being vented to atmosphere;
   d) whereby air pressure expelled from said CPR bag chamber is sensed in said upper chamber causing said movable wall to move downwardly against force of said spring, said pointer thereby rotating into alignment with an indicium representative of pressure in said upper chamber.

2. The combination of claim 1, wherein said movable wall is a diaphragm.

3. The combination of claim 1, wherein said pointer is located within said upper chamber.

4. The combination of claim 3, wherein said cap is transparent.

5. The combination of claim 1, wherein said restricted passageway includes a first passageway portion integral with said patient breathing valve and a second passageway portion integral with said manometer.

6. The combination of claim 1, wherein said manometer is disposable.

7. The combination of claim 1, wherein said CPR bag is disposable.

8. The combination of claim 7, wherein said manometer is disposable.

9. The combination of claim 1, wherein said patient breathing valve has a recess sized to removably receive a portion of said manometer housing therein.

10. In combination with a breathing tube including a mouthpiece, a passage, an outlet and a sensing port fluidly connected to said passage, a manometer for sensing and displaying pressure in said passage comprising:
   a) a housing having an upper chamber and a lower chamber separated by a movable wall, said movable wall carrying a stem coupling having an opening with an outwardly extending groove and a bottom surface engaging a compression spring within said lower chamber;
   b) said upper chamber being upwardly closed by a cap having pressure indicating indicia thereon, and said cap having a pointer mechanism rotatably mounted thereon and including a pointer alignable with said indicia to indicate pressure in said upper chamber, said pointer mechanism including a downwardly depending actuator stem having a spiral-shaped projection thereon, said actuator stem inserted into said stem coupling opening with said spiral-shaped projection engaged within said groove, whereby reciprocations of said stem coupling translate to rotations of said pointer;
   c) said upper chamber being fluidly connected to said sensing port via a restricted passageway and said lower chamber being vented to atmosphere;
   d) whereby pressure at said sensing port is sensed in said upper chamber causing said movable wall to move downwardly against force of said spring, said pointer thereby rotating into alignment with an indicium representative of pressure in said upper chamber.

11. The combination according to claim 10 wherein the breathing tube and manometer are disposable.

12. The combination according to claim 10 wherein the breathing tube and manometer are substantially made from a hardened plastic.

13. A manometer for sensing and displaying air pressure in combination with a CPR bag or a patient breathing tube, the manometer comprising
   a) a housing having an upper chamber and a lower chamber separated by a movable wall, said movable wall carrying a stem coupling having an opening with an outwardly extending groove and a bottom surface engaging a compression spring within said lower chamber;
   b) said upper chamber being upwardly closed by a cap having pressure indicating indicia thereon, and said cap having a pointer mechanism rotatably mounted thereon and including a pointer alignable with said indicia to indicate pressure in said upper chamber, said pointer mechanism including a downwardly depending actuator stem having a spiral-shaped projection thereon, said actuator stem inserted into said stem coupling opening with said spiral-shaped projection engaged within said groove, whereby reciprocations of said stem coupling translate to rotations of said pointer;

c) said upper chamber being fluidly connected to a source of air from the CPR bag or patient breathing tube via a restricted passageway and said lower chamber being vented to atmosphere;

d) whereby pressure at a sensing port is sensed in said upper chamber causing said movable wall to move downwardly against force of said spring, said pointer thereby rotating into alignment with an indicium representative of pressure in said upper chamber.

14. The manometer according to claim 13 wherein said movable wall is a diaphragm.

15. The manometer according to claim 13 wherein the manometer is made substantially of hardened plastic and is disposable after one patient's use.

* * * * *